United States Patent [19]

Wiley

[11] 4,300,394
[45] Nov. 17, 1981

[54] SONIC WAVE TRAVEL TIME MEASURING SYSTEM

[75] Inventor: Bruce F. Wiley, Bartlesville, Okla.

[73] Assignee: Phillips Petroleum Co., Bartlesville, Okla.

[21] Appl. No.: 42,164

[22] Filed: May 24, 1979

[51] Int. Cl.³ .......................................... G01N 29/00
[52] U.S. Cl. ................................................... 73/597
[58] Field of Search ................. 73/597, 610, 613, 614, 73/618, 629, 1 DV

[56] References Cited

U.S. PATENT DOCUMENTS

| | | | |
|---|---|---|---|
| 3,504,532 | 4/1970 | Muenow et al. | 73/597 |
| 3,774,444 | 11/1973 | Kent | 73/597 |
| 3,848,460 | 11/1974 | Bantz et al. | 73/597 |
| 3,985,022 | 10/1976 | Dileo et al. | 73/629 |
| 3,995,501 | 12/1976 | Wiley | 73/597 |
| 4,022,058 | 5/1977 | Brown | 73/597 |
| 4,114,455 | 9/1978 | Walker | 73/597 |

*Primary Examiner*—Stephen A. Kreitman

[57] ABSTRACT

A time measuring system is provided which automatically compensates for the propagation time of electrical pulses and sonic waves through the apparatus associated with a core analysis system. In this manner, the time required for a sonic pulse to propagate through a core sample is measured exactly and the velocity of the sonic wave through the core sample is calculated based on the propagation time and the sample length.

11 Claims, 1 Drawing Figure

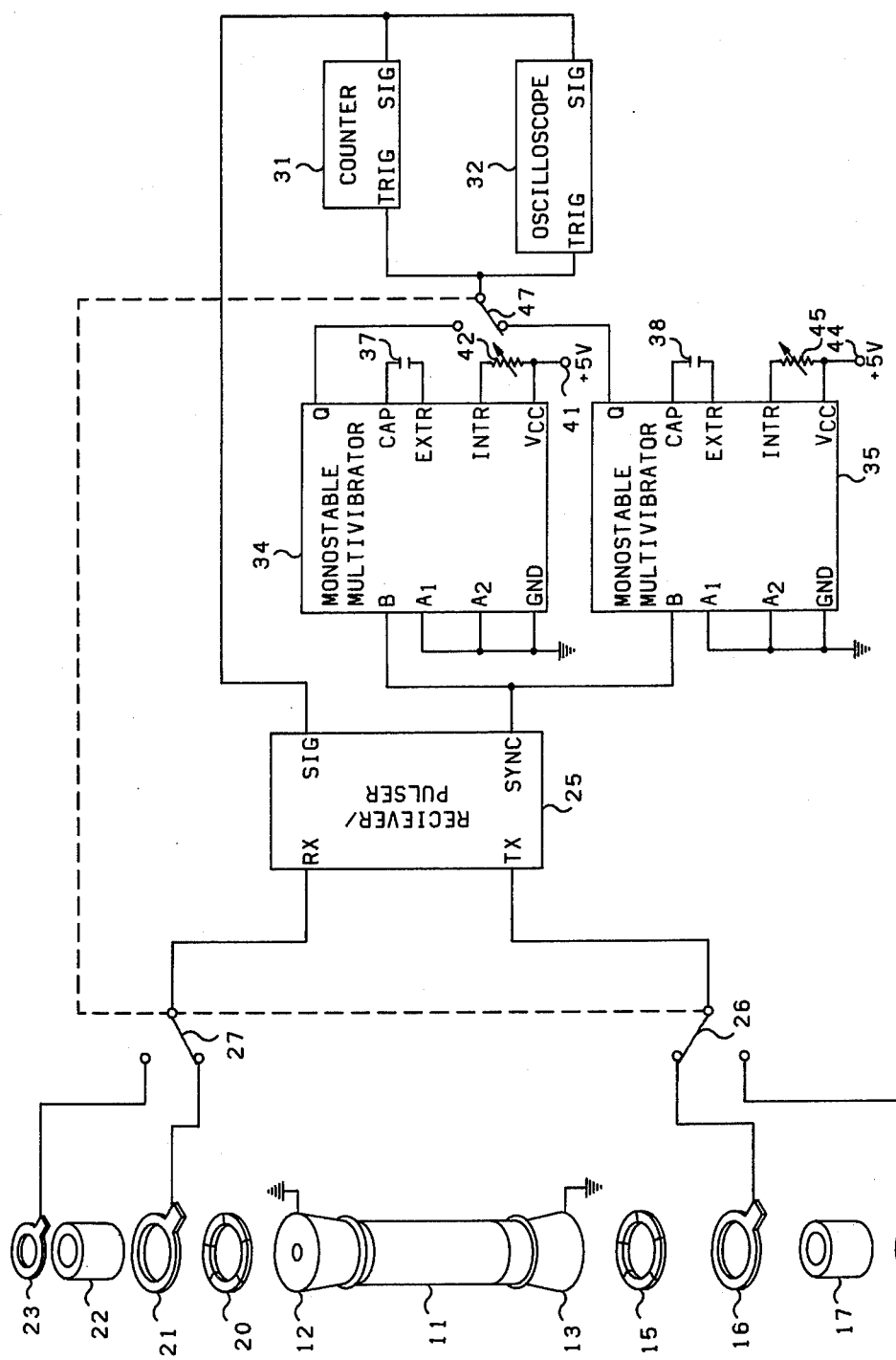
F/G. /

SONIC WAVE TRAVEL TIME MEASURING SYSTEM

This invention relates to core analysis. In a particular aspect this invention relates to method and apparatus for measuring the time required for a sonic pulse to propagate through a core sample.

In the science of core analysis, a compressional or shear sonic wave is caused to enter one end of a core sample. The propagation time for the sonic wave through the core sample is measured. Based on the measured time and the sample length, the velocity of the sonic wave through the core sample is calculated. Various characteristics of the core sample can be determined from the velocity of the sonic wave through the core sample.

U.S. Pat. No. 3,995,501 discloses apparatus which can be utilized to introduce shear or compressional waves into a core sample. A pulser is utilized to generate an electrical pulse which travels through inductive lines to a shear or compressional transducer where the electrical pulse is converted to a mechanical or pressure pulse which results in a shear or compressional wave propagating through the core sample. The sonic save is received at the opposite end of the core sample from which the sonic wave was introduced and reconverted back to an electrical pulse. The electrical pulse is provided to a receiver through inductive lines.

The period of time which elapses between the time when the electrical pulse is initiated and the time when the electrical pulse is received (transmit-to-receive time) may be considered the propagation time for the sonic wave through the core sample. However, inherent delays are present in the apparatus which result in errors if the transmit-to-receive time is used. Delays in the inductive lines and delays in the conversion of the electrical pulse to a mechanical or pressure pulse must be compensated for. Also delays between the pieces which contact the core sample and the transducers must be compensated for.

In the past, it has been common to measure the various delays in the system and subtract these delays from the measured transmit-to-receive time. However, it is always advantageous where a large number of samples are being analyzed to have an automated system. It is thus an object of this invention to provide method and apparatus for measuring the time required for a sonic pulse to propagate through a core sample. In particular, it is an object of this invention to provide method and apparatus for automatically compensating for delays caused by apparatus in a core analysis system.

In accordance with the present invention, method and apparatus is provided whereby an electrical pulse is provided to either a shear or compressional transducer. This sonic wave propagates through the core sample, is received, converted back to electrical form, and provided to a receiver. When the electrical signal is received, the receiver provides a signal (stop count signal) to a counter which stops a counter-timer. The stop count signal from the receiver is also supplied to an oscilloscope.

At the same time that the electrical pulse is transmitted to either the compressional or shear transducers, a sync pulse is provided from the transmitter to a pair of monostable multivibrators. The output of each of the monostable multivibrators is tied to the triggering input of the counter-timer and the oscilloscope. One of the monostable multivibrators is utilized to compensate for the delay time for a compressional wave while the other is utilized to compensate for the delay time for a shear wave.

In operation, the core sample is removed from the core analysis apparatus and the core contact pieces are placed in contact. An electrical pulse is provided to the shear wave transducer. The delay in a first monostable multivibrator is adjusted until the counter-timer reads zero. This procedure is then repeated for the compressional wave using the second monostable multivibrator. In this manner, the inherent delays in the apparatus are compensated for and, when the core sample is inserted, the count displayed by the counter-timer will be representative only of the propagation time of either the shear or compressional wave through the core sample.

The oscilloscope is utilized to insure that the counter-timer is being triggered at the same point on the received electrical signal. Attenuation or gain is utilized to insure that the signal received by the counter-timer is the same for different types of core samples and even if no core sample is in place. In this manner, the accuracy of the time measurement system is increased.

Other objects and advantages of the invention will be apparent from the foregoing brief description of the invention and the claims as well as from the detailed description of the drawing in which:

FIG. 1 is a schematic diagram of the time measurement system of the present invention.

The present invention is described in terms of a particular core analysis system. However, the invention is applicable to any core analysis system in which it is desired to compensate for delays caused by various pieces of apparatus in the core analysis system.

The invention is also described in terms of particular apparatus. However, the invention is applicable to different types of apparatus which accomplish the purpose of the present invention.

Referring now to the drawing, a core sample 11 is illustrated between the contact pieces 12 and 13. A shear transducer 15 will be in contact with the contact piece 13. The shear transducer 15 has a hole in the center thereof sufficiently large to allow the compressional transducer 17 to also be in contact with the contact piece 13. The shear transducer 15 has an electrode 16 associated therewith. The compressional transducer 17 has an electrode 18 associated therewith. A shear transducer 20 will be in contact with the contact piece 12. The shear transducer 20 has a hole in the center thereof sufficiently large to allow the compressional transducer 22 to also be in contact with the contact piece 12. The shear transducer 20 has an electrode 21 associated therewith. The compressional transducer 22 has an electrode 23 associated therewith.

The various elements of the core analysis apparatus illustrated would be in close contact or would be separated only by an oil film. The elements have been shown in an exploded view for the sake of simplicity and better illustration of the present invention.

The electrode 16 is connected to the transmit output of the receiver/pulser 25 through the switching means 26. In like manner, the electrode 18 is connected through switching means 26 to the transmit output of the receiver/pulser 25. The electrode 21 is connected to the receive input of the receiver/pulser 25 through the switching means 27. In like manner, the electrode 23 is connected to the receive input of the receiver/pulser 25 through switching means 27.

The signal output of the receiver/pulser 25 is tied to the signal input of the counter 31 and the oscilloscope 32. The sync output of the receiver/pulser 25 is electrically connected to the B input of the monostable multivibrators 34 and 35. The $A_1$, $A_2$ and ground (GND) inputs of the monostable multivibrator 34 and the monostable multivibrator 35 are tied to ground. The capacitance (CAP) terminal and the external resistance (EXTR) terminal of the monostable multivibrator 34 are electrically connected through capacitor 37. In like manner, the capacitance terminal and the external resistance terminal of the monostable multivibrator 35 are electrically connected through capacitor 38. The internal resistance (INTR) terminal and the $V_{cc}$ terminal of the monostable multivibrator 34 are electrically connected through variable resistance 42. The Vcc terminal of the monostable multivibrator 34 is directly connected to the +5 volt power supply 41. The internal resistance terminal of the monostable multivibrator 34 is connected to the +5 volt power supply 4 through variable resistance 42. In like manner, the internal resistance and $V_{cc}$ terminals of the monostable multivibrator 35 are electrically connected through the variable resistance 45. The Vcc terminal of the monostable multivibrator 35 is directly connected to the +5 volt power supply 44. The internal resistance terminal of the monostable multivibrator 35 is connected to the +5 volt power supply 44 through the variable resistance 45. The Q output (which is a positive going square wave referred to hereinafter as a delayed sync pulse) of the monostable multivibrator 34 is tied through switching means 47 to the negative slope trigger input of the counter-timer 31 and the oscilloscope 32. In like manner, the Q output (delayed sync pulse) of the monostable multivibrator 35 is tied through switching means 47 to the negative slope trigger input of the counter-timer 31 and the oscilloscope 32.

Switching means 26, 27 and 47 constitutes a single three-pole double throw switch. All of the switches 26, 27 and 47 will either be in the position illustrated in FIG. 1 or will be in the opposite position.

To adjust the time measurement system illustrated in FIG. 1, the core sample 11 is first removed and the contact pieces 12 and 13 are placed in contact. An electrical pulse is then transmitted from the receiver/pulser 25 to the shear transducers. At the same time that the pulse is transmitted, a sync pulse is provided to the monostable multivibrators 34 and 35. With the switches in the position shown, the monostable multivibrator 35 is utilized to compensate for delays for the shear wave.

The electrical pulse from the receiver/pulser is converted to a shear wave which propagates to the shear receiver 21, is converted to an electrical pulse, and is provided to the receive input of the receiver/pulser 25. When the signal is received at the receive input of the receiver/pulser 25, a signal is provided from the output of the receiver/pulser 25 to the signal input of the counter-timer 31 and the signal input of the oscilloscope 32. The signal provided from the signal output of the receiver/pulser 25 will be proportional to the strength of the received signal. The strength of this signal is monitored on the oscilloscope 32. The receiver/pulser attenuation or gain is adjusted such that the signal will have a preferred peak voltage 0.4 volts. The counter-timer 31 is adjusted such that it will stop counting when the signal reaches a voltage level of 0.2 volts, preferably. After the gain or attenuation of the receiver/pulser 25 is adjusted, electrical pulses are transmitted from the transmitter terminal of the receiver/pulser 25 and the variable resistance 45 associated with the monostable multivibrator 35 is adjusted until the time on the counter-timer 31 reads zero. In this manner, inherent delays in the apparatus illustrated in FIG. 1 are compensated for. When the core 11 is again inserted between the contact pieces 12 and 13, and a pulse is transmitted from the receiver/pulser 25, the time displayed on the counter-timer 31 will be representative only of the propagation time of the shear wave through the core sample 11.

When the core sample is inserted, the attenuation or gain of the receiver/pulser must again be adjusted using the oscilloscope 32 so that the peak voltage of the signal output from the receiver/pulser 25 will again be 0.4 volts so that the counter-timer 31 will again be stopped at the same voltage level. This compensates for the finite rise time of the received signal.

The above procedure is repeated with switching means 26, 27 and 47 switched to the opposite position from that illustrated in FIG. 1. The monostable multivibrator 34 is utilized to compensate for the delay time for the compressional wave. Variable resistance 42 is adjusted to make the time displayed by the counter-timer 31 equal to zero when the contact pieces 12 and 13 are in contact. The oscilloscope 32 is again used to adjust the peak voltage of the signal output from the receiver/pulser 25.

The time measurement system illustrated in FIG. 1 provides a automatic method for compensating for delays caused by the apparatus in a core analysis system. The accuracy of the time measurement system is improved and the repeatability of measurements is increased. Also, a large number of core samples can be analyzed more quickly and a large number of measurements on a single sample can be made with greater speed and accuracy.

The invention has been described in terms of its presently preferred embodiment as is illustrated in FIG. 1. As has been previously stated, many different circuit configurations could be utilized to perform the functions of the present invention. Specific components which are available commercially and which can be used in the practice of the invention as illustrated in FIG. 1 are as follows:

| Receiver/Pulser 25 | Panametrics Pulser/Receiver Model 505PR Panametrics, Inc. |
|---|---|
| Monostable Multivibrators 34 and 35 | 74121 National Semiconductor |
| Counter-timer 31 | Model 1952B John Fluke Mfg. Co. |
| Oscilloscope 32 | Model 5440 Tektronix, Inc. |

While the invention has been described in terms of the presently preferred embodiment, reasonable variations and modifications are possible by those skilled in the art, within the scope of the described invention and the appended claims.

That which is claimed is:

1. Apparatus comprising:
an electrical pulser means;
first transducer means for introducing a sonic wave into a core sample;
means for transmitting an electrical pulse from said electrical pulser means to said first transducer means, said first transducer means introducing a sonic wave into said core sample in response to the transmitted electrical pulse;
an electrical receiver means;
second transducer means for receiving said sonic wave after said sonic wave propagates through said core sample, said second transducer means providing an electrical pulse to said receiver means when a sonic wave is received by said second transducer means;
a timing means;
a delay means;
means for supplying a sync pulse from said electrical pulser means to said delay means when the electrical pulse is transmitted from said electrical pulser means to said first transducer means;
means for supplying a delayed sync pulse from said delay means to the trigger input of said timing means to thereby initiate said timing means;
means for supplying a stop count signal from said receiver means to said timing means, when the electrical pulse from said second transducer means is received by said receiver means, to thereby stop said timing means, said delay means being adjusted in such a manner that the time on said timing means is representative only of the propagation time of said sonic wave through said core sample;
an oscilloscope means;
means for providing said stop count signal to said oscilloscope means; and
means for adjusting the amplitude of said stop count signal, the amplitude of said stop count signal being adjusted until a desired amplitude is displayed on said oscilloscope means.

2. Apparatus in accordance with claim 1 wherein said first transducer means is a shear wave transducer means, said sonic wave is a shear wave, and said second transducer means is a shear wave receiver means.

3. Apparatus in accordance with claim 1 wherein said first transducer means is a compressional wave transducer means, said sonic wave is a compressional wave, and said second transducer means is a compressional wave transducer means.

4. Apparatus in accordance with claim 1 wherein said delay means is a monostable multivibrator.

5. In a core analysis system in which a timer is utilized to measure the propagation time of a sonic wave through a core sample, a method for accurately measuring the propagation time of said sonic wave through said core sample comprising the steps of automatically delaying the initiation of said timer so as to automatically compensate for inherent time delays in said core analysis system, the time on said timer being representative only of the propagation time of said sonic wave through said core sample and adjusting the amplitude of the electrical signal which stops said timer so as to compensate for the properties of different core samples or no core sample.

6. A method in accordance with claim 5 wherein said sonic wave is a shear wave.

7. A method in accordance with claim 5 wherein said sonic wave is a compressional wave.

8. A method for calibrating a time measurement system in which a triggering pulse to a timer is delayed to compensate for time delays in a core analysis system comprising the steps of:
placing the transmit and receive core contact pieces of said core analysis system in contact;
introducing a sonic wave into said transmit core contact piece, in response to an electrical signal, said triggering pulse being transmitted through a delay means to a timer at the same time said electrical signal is transmitted;
providing a stop count signal to said timer when said sonic wave propagates through said core analysis system;
adjusting said delay means in such a manner that said timer reads zero when said transmit core contact piece is in contact with said receive core contact piece and a sonic wave is introduced into said transmit core contact piece; and
adjusting the amplitude of said stop count signal to a desired amplitude.

9. A method in accordance with claim 8 wherein said sonic wave is a shear wave.

10. A method in accordance with claim 8 wherein said sonic wave is a compressional wave.

11. A method in accordance with claim 8 wherein said delay means is a monostable multivibrator.

* * * * *